(12) United States Patent
Simard (10) Patent No.: US 11,390,672 B2
(45) Date of Patent: Jul. 19, 2022

(54) ARTHRITIS TREATMENT

(71) Applicant: Janssen Biotech, Inc., Horsham, PA (US)

(72) Inventor: John Simard, Austin, TX (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 16/530,667

(22) Filed: Aug. 2, 2019

(65) Prior Publication Data

US 2019/0352391 A1 Nov. 21, 2019

Related U.S. Application Data

(63) Continuation of application No. 15/235,263, filed on Aug. 12, 2016, now abandoned, which is a continuation of application No. 13/162,705, filed on Jun. 17, 2011, now abandoned.

(60) Provisional application No. 61/356,176, filed on Jun. 18, 2010.

(51) Int. Cl.
*C07K 16/24* (2006.01)
*A61K 39/00* (2006.01)

(52) U.S. Cl.
CPC ...... *C07K 16/245* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,634,664 A | 1/1987 | Oestberg | |
| 4,965,198 A | 10/1990 | Yamasaki | |
| 4,968,607 A | 11/1990 | Dower | |
| 5,034,316 A | 7/1991 | Weisbart | |
| 5,168,062 A | 12/1992 | Stinski | |
| 5,231,024 A | 7/1993 | Moeller | |
| 5,585,089 A | 12/1996 | Queen | |
| 5,654,407 A | 8/1997 | Boyle | |
| 5,693,762 A | 12/1997 | Queen | |
| 5,792,838 A | 8/1998 | Smith | |
| 5,795,967 A | 8/1998 | Aggarwal | |
| 5,932,188 A | 8/1999 | Snow | |
| 5,959,085 A * | 9/1999 | Garrone | C07K 16/245 435/252.3 |
| 6,090,382 A | 7/2000 | Salfeld | |
| 6,140,470 A | 10/2000 | Garen | |
| 6,623,736 B2 | 9/2003 | Tobinick | |
| 7,105,183 B2 | 9/2006 | McGrath | |
| 7,718,674 B2 | 5/2010 | Aberg | |
| 8,034,337 B2 | 10/2011 | Simard | |
| 8,034,377 B2 * | 10/2011 | Brune | C07D 213/30 424/452 |
| 8,242,074 B2 * | 8/2012 | Simard | A61P 29/00 514/12.2 |
| 8,388,956 B2 | 3/2013 | Simard | |
| 8,388,969 B2 | 3/2013 | Simard | |
| 8,398,966 B2 | 3/2013 | Wu | |
| 8,546,331 B2 * | 10/2013 | Simard | A61P 9/00 514/12.2 |
| 8,679,489 B2 | 3/2014 | Simard | |
| 8,697,689 B2 | 4/2014 | Cid-Nunez | |
| 8,784,817 B2 | 7/2014 | Simard | |
| 9,416,172 B2 | 8/2016 | Simard | |
| 9,840,558 B2 | 12/2017 | Simard | |
| 2002/0022720 A1 | 2/2002 | Le | |
| 2002/0044919 A1 | 4/2002 | Yu | |
| 2003/0004061 A1 | 1/2003 | Kraemer | |
| 2003/0023205 A1 | 1/2003 | Botich | |
| 2003/0026806 A1 * | 2/2003 | Witte | C07K 16/245 424/145.1 |
| 2003/0040617 A9 | 2/2003 | Rosen | |
| 2003/0175832 A1 | 9/2003 | Marton | |
| 2003/0232054 A1 | 12/2003 | Tang | |
| 2004/0097712 A1 | 5/2004 | Varnum | |
| 2004/0185514 A1 | 9/2004 | Frostegard | |
| 2004/0224893 A1 | 11/2004 | Wang | |
| 2005/0005401 A1 | 1/2005 | Bae | |
| 2005/0054019 A1 | 3/2005 | Michaud | |
| 2005/0129699 A1 | 6/2005 | Salcedo | |
| 2005/0147603 A1 | 7/2005 | Smith | |
| 2005/0276807 A1 | 12/2005 | Skurkovich | |
| 2006/0127407 A1 | 6/2006 | Chen | |
| 2006/0159775 A1 | 7/2006 | McGrath | |
| 2007/0071675 A1 | 3/2007 | Wu | |
| 2008/0050310 A1 | 2/2008 | Ebens | |
| 2009/0123415 A1 | 5/2009 | Simard | |
| 2009/0191149 A1 | 7/2009 | Simard | |

(Continued)

FOREIGN PATENT DOCUMENTS

| | | |
|---|---|---|
| AU | 2007202323 | 6/2007 |
| CA | 2426384 | 4/2003 |

(Continued)

OTHER PUBLICATIONS

Kurzrock et al, OncoImmunology Journal, 2019, vol. 8, No. 3, pp. 1-7.

Niki, Y, et al. Membrane-associated IL-1 contributes to chronic synovitis and cartilage destruction in human IL-1 alpha transgenic mice. J. Immunology, 2004, vol. 172, No. 1, p. 577-584.

Svenson, M. et al., Binding of Cytokines to Pharmaceutically Prepared Human Immunoglobulin, J. Clin. Invest., Nov. 1993, vol. 92:2533-2539.

Chang, C.H. et al., "Interleukin-1alpha released from epithelial cells after adenovirus type 37 infection activates intercellular adhesion molecule 1 expression on human vascular endothelial cells," Journal of Virology, Jan. 2002, vol. 76, No. 1:427-431.

Lundberg, Ingrid et al., "Cytokine production in muscle tissue of patients with idiopathic inflammatory myopathies," Arthritis & Rheumatism, May 1997, vol. 40, No. 5:865-874.

(Continued)

*Primary Examiner* — Marianne P Allen
(74) *Attorney, Agent, or Firm* — Ice Miller LLP (57) ABSTRACT

Administration of a monoclonal Ab (mAb) that specifically targets IL-1α is useful to treating articular and extra-articular symptoms of arthritis.

7 Claims, 5 Drawing Sheets

(56) References Cited

U.S. PATENT DOCUMENTS

| | | |
|---|---|---|
| 2009/0215992 A1 | 8/2009 | Wu |
| 2009/0258070 A1 | 10/2009 | Burnier |
| 2009/0291081 A1 | 11/2009 | Hsieh |
| 2009/0298096 A1* | 12/2009 | Simard ............... A61P 43/00 435/7.21 |
| 2010/0040574 A1 | 2/2010 | Simard |
| 2010/0047239 A1 | 2/2010 | Wu |
| 2010/0068212 A1 | 3/2010 | Simard |
| 2010/0221179 A1 | 9/2010 | Hsieh |
| 2011/0008282 A1 | 1/2011 | Simard |
| 2011/0142761 A1 | 6/2011 | Wu |
| 2011/0311547 A1 | 12/2011 | Simard |
| 2012/0015384 A1 | 1/2012 | Simard |
| 2012/0045444 A1 | 2/2012 | Simard |
| 2012/0231012 A1 | 9/2012 | Simard |
| 2012/0251548 A1 | 10/2012 | Simard |
| 2012/0275996 A1 | 11/2012 | Hsieh |
| 2013/0039921 A1 | 2/2013 | Simard |
| 2013/0078258 A1 | 3/2013 | Simard |
| 2013/0195877 A1 | 8/2013 | Simard |
| 2013/0287788 A1 | 10/2013 | Simard |
| 2014/0086933 A1 | 3/2014 | Simard |
| 2015/0024031 A1 | 1/2015 | Rabinow |
| 2016/0024190 A1 | 1/2016 | Ohsawa |

FOREIGN PATENT DOCUMENTS

| | | |
|---|---|---|
| CN | 1431909 A | 7/2003 |
| CN | 1662557 | 8/2005 |
| CN | 101472948 | 7/2009 |
| EP | 0267611 | 5/1988 |
| EP | 0659766 | 6/1995 |
| JP | 2004285057 | 10/2004 |
| WO | 9006371 | 6/1990 |
| WO | 9524917 A1 | 9/1995 |
| WO | 9635719 | 11/1996 |
| WO | 0120828 | 3/2001 |
| WO | 0233094 | 4/2002 |
| WO | 2004100987 | 11/2004 |
| WO | 2006001967 | 1/2006 |
| WO | 2007015128 | 2/2007 |
| WO | 2007039552 | 4/2007 |
| WO | 2007120828 | 10/2007 |
| WO | 2007132338 | 11/2007 |
| WO | 2007135546 | 11/2007 |
| WO | 2009148575 A1 | 12/2009 |
| WO | 2010030979 | 3/2010 |
| WO | 2010087972 | 8/2010 |
| WO | 2011159976 | 12/2011 |
| WO | 2012027324 | 3/2012 |
| WO | 2012034039 | 3/2012 |
| WO | 2012135812 | 10/2012 |
| WO | 2013043973 | 3/2013 |
| WO | 2014055541 | 4/2014 |
| WO | 2014055544 | 4/2014 |

OTHER PUBLICATIONS

Tsunoda, Yasuaki et al., "Immunohistochemical study of cytokines and extracellular matrices at invasive sites of human colon cancers," Biotherapy, May 1996, vol. 10, No. 5:789-790; Abstract only.

Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.

Yanni, G. et al: "Intramuscular gold decreases cytokine expression and macrophage numbers in the rheumatoid synovial membrane," Annals of the Rheumatic Diseases, 1994, vol. 53:315-322.

Dekker, S.K. et al: "Characterization of interleukin-1alpha-induced melanoma cell motility: inhibition by type I and type II receptor-blocking monoclonal antibodies," Melanoma Research, 1997, vol. 7:223-230.

Kleiman, et al: "Invasion assays," Current Protocols in Cell Biology, 2001, 12.2.1-12.2.5.

Sawai, H. et al: "Interleukin-1 alpha enhances the aggressive behavior of pancreatic cancer cells by regulating the alpha 6 beta I-integrin and urokinase plasminogen activator receptor expression," MC Cell Biology, 2006:1-13.

Lewis, Anne M. et al: "Interleukin-I and cancer progression: the emerging role of interleukin-1 receptor antagonist as a novel therapeutic agent in cancer treatment," Journal of Translational Medicine, 2006, vol. 4, No. 48:1-12.

Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.

Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.

Voronov, E. et al: "IL-1 is required for tumor invasiveness and angiogenesis," PNAS, 2003, vol. 100, No. 5:2645-2650.

Uefuji, K. et al: "Increased expression of interleukin-1alpha and cyclooxygenase-2 in human gastric cancer: a possible role in tumor progression," 2005, Anticancer Research, vol. 25:3225-3230.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

Bendtzen, Klaus et al., High-Avidity Autoantibodies to Cytokines, Trends Immunology Today, May 1998, vol. 19, No. 5 209, 3 pages.

Bendtzen, Klaus et al., Detection of Autoantibodies to Cytokines, Molecular Biotechnology, 2000, vol. 14, 14 pages.

Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.

Dinarello, Charles A., Modalities for reducing interleukin 1 activity in disease, TiPS, May 1993 vol. 14:155-159.

Dinarello, Charles A. et al., Anticytokine strategies in the treatment of the systemic inflammatory response syndrome, The Journal of the American Medical Association, Apr. 1993, vol. 269, No. 14:1829-1835.

Dinarello, Charles A., Biologic basis for interleukin-1 in disease, Blood, Mar. 1996, vol. 87, No. 6:2095-2147.

Dinarello, Charles A., Therapeutic strategies to reduce IL-1 activity in treating local and system inflammation, Current Opinion in Pharmacology, 2004, vol. 4:378-385.

Larrick, James W. et al., Prospects for the therapeutic use of human monoclonal antibodies, Journal of Biological Response Modifiers, 1986, vol. 5:379-393.

Griffiths, Andrew D. et al., Human anti-self antibodies with high specificity from phage display libraries, the EMBO Journal, 1993, vol. 12, No. 2:725-734.

Satoh, H. et al., Characterization of anti-IL-1alpha autoantibodies in the sera from healthy humans, Immunopharmacology, 1994, vol. 27:107-118.

Hansen, M. B. et al., Sex- and age-dependency of IgG auto-antibodies against IL-1 alpha in healthy humans, European Journal of Clinical Investigation, 1994, vol. 24:212:218.

Jouvenne, P. et al., High levels of neutralizing autoantibodies against IL-1 alpha are associated with a better prognosis in chronic polyarthritis: a follow-up study, Scand. J. Immunol., 1997, vol. 46:413-418.

Lindqvist, E. et al., Prognostic laboratory markers of joint damage in rheumatoid arthritis, Ann Rheum Dis, 2005, vol. 64:196-201.

Ogushi, F. et al., Autoantibodies to IL-1 alpha in sera from rapidly progressive idiopathic pulmonary fibrosis, The Journal of Medical Investigation, 2001, vol. 48:181-189.

Ross, Christian, et al., High avidity IFN-neutralizing antibodies in pharmaceutically prepared human IgG, J. Clin. Invest., May 1995, vol. 95:1974-1978.

Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.

(56) References Cited

OTHER PUBLICATIONS

Suzuki, Hiroshi et al., Demonstration of Neutralizing Autoantibodies against II-1alpha IN sera from patients with rheumatoid arthritis, The Journal of Immunology, Oct. 1, 1990, vol. 145, No. 7:2140-2146.
Svenson, M. et al., IgG Autoantibodies against Interleuking 1alpha in sera of normal individuals, Scand. J. Immunol., 1989, vol. 29:489-492.
Svenson, M. et al., Effects of human anti-IL-1 alpha autoantibodies on receptor binding and biological activities of IL-1 alpha, Cytokine, Mar. 1992, vol. 4, No. 2:125-133.
Svenson, M. et al., Distribution and characterization of autoantibodies to interleukin 1 alpha in normal human sera, Scand. J. Immunol., 1990, vol. 32:695-701.
Svenson, M. et al., Antibody to granulocyte-macrophage colony-stimulating factor is a dominant anti-cytokine activity in human IgG preparations, Blood, Mar. 1998, vol. 91, No. 6:2054-2061.
Svenson M, et al. Cytokine vaccination: neutralising IL-1 alpha autoantibodies induced by immunisiation with homologous IL-1alpha. Journal of Immunological Methods, 2000, vol. 236, No. 1-2, p. 1-8.
Waehre et al., Increased expression of interleukin-1 in coronary artery disease with downregulatory effects of HMG-CoA reductase inhibitors, «circ.ahajournals.org», downloaded on Jan. 15, 2008:1966-1972.
Clinton Steven K. et al., Interleukin-1 gene expression in rabbit vascular tissue in vivo, American Journal of Pathology, Apr. 1991, vol. 138, No. 4:1005-1014.
Von Der Thusen, Jan H., et al., Interleukins in atherosclerosis: Molecular pathways and therapeutic potential, Pharmacol Rev, 2003, vol. 55, No. 1:133-166.
Kasahara, T. et al., Preparation and characterization of polyclonal and monoclonal antibodies against human interleukin 1 alpha (IL 1 alpha), The Journal of Immunology, Mar. 1987, vol. 138, No. 6:1804-1812.
Merhi-Soussi, F. et al., Interleukin-1 plays a major role in vascular inflammation and atherosclerosis in male apolipoprotein E-knockout mice, Cardiovacular Research, 2006, vol. 66:583-593.
Ross, C. et al., Increased in vivo antibody activity against interferon alpha, interleuking-1alpha, and interleukin-6 after high-dose Ig therapy, Blood, Sep. 1997, vol. 90, No. 6:2376-2380.
Ito, R. et al., Interleukin 1 alpha acts as an autocrine growth stimulator for human gastric carcinoma cells, Cancer Research, Sep. 1993, vol. 53:4102-4106.
Shirakawa, F. et al., Autocrine stimulation of interleukin 1alpha in the growth of adult human T-cell leukemia cells, Cancer Research, Mar. 1989, vol. 49:1143-1147.
Apte, Ron N., et al., Effects of micro-environment- and malignant cell-derived interleukin-1 in carcinogenesis, tumour invasiveness and tumour-host interactions, European Journal of Cancer, 2006, vol. 42:751-759.
Dinarello, Charles A., The role of interleukin-1 in disease, The New England Journal of Medicine, 1993, vol. 328, No. 2:106-113.
Wake, R. et al., Gender differences in ischemic heart disease, Recent Patents on Cardiovascular Drug Discovery, 2009, vol. 4:234-240.
Mariotti, Massimo et al., Iterleukin 1 alpha is a marker of endothelial cellular senescent, Immunity & Ageing, Research, Apr. 2006, vol. 3, No. 4:1-6.
McHale, Julie F. et al., TNF-alpha and IL-sequentially induce endothelial ICAM-1 and VCAM-1 expression in MRL/lpr lupus-prone mice, The American Association of Immunologists, 1999, vol. 163:3993-4000.
Sandborg, Christy L. et al., Modulation of IL-1 alpha, IL-1 beta, and 25K Mr Non-IL-1 activity released by human mononuclear cells, Journal of Leukocyte Biology, 1989, vol. 46:417-427.
GenBank entry AY510107.1, Homo sapiens 9F11 monoclonal IgM antibody light chain mRNA, complete cds, 2005 (retrieved from the Internet on Apr. 23, 2010, <http://www.ncbi.nlm.nih.gov/nuccore/41388185>, 1 page.
Sunahara, N. et al., Differential determination of recombinant hum interleukin-1 alpha and its deamidated derivative by two sandwich enzyme immunoassays using monoclonal antibodies. Comparison with a polyclonal antibody-based competitive enzyme immunoassay., J Immunol Methods, 1989, vol. 119:75-82 (Abstract only).
Miossec, P., Anti-interleukin 1 alpha autoantibodies, Ann Rheum Dis, 2002, vol. 61:577-579.
Horai, R. et al., Production of mice deficient in genes for interleukin (IL)-1 alpha, IL-1 beta, IL-1 alpha/beta, and IL-1 receptor antagonist shows that IL-1 beta is crucial in turpentine-induced fever development and glucocorticoid secretion, J. Exp. Med, 1998, vol. 187, No. 9:1463-1475.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Braddock, M. et al., Therapeutic potential of targeting IL-1 and IL-18 in inflammation, Expert Opin. Biol. Ther., 2004, vol. 4, No. 6:8476-860.
Eugui, E.M. et al., Antibodies against membrane interleukin 1 alpha activate accessory cells to stimulate proliferation of T lymphocytes, Proc. Natl. Acad. Sci USA, 1990, vol. 87:1305-1309.
Janeway, C.A., Jr. et al., The induction, measurement, and manipulation of the immune response, ImmunoBiology, the Immune System in Health and Disease, 1997, Third Edition, 8 pages.
Kaji, Mitsuhito et al., E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.
Jefferis, Roy: "Antibody therapeutics: isotype and glycoform selection," Expert Opin. Biol. Ther. (2007) 7 (9):1401-1413.
Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.
Buchan, G. et al: "Interleukin-1 and tumour necrosis factor mRNA expression in rheumatoid arthritis: prolonged production of IL-1alpha," Clin. Exp. Immunol. (1988), vol. 73:449-455.
Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.
Chen, Z. et al: "Effects of interleukin-1 alpha, interleukin-1 receptor antagonist, and neutralizing antibody on proinflammatory cytokine expression by human squamous cell carcinoma lines," Cancer Research (1998), vol. 58:3668-3676.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.
Chamberlain, R.S. et al., Innovations and strategies for the development of anticancer vaccines, Exp. Opin. Pharmacother., 2000, vol. 1(4)603-614.
Janik, John E. et al: "Interleukin 1 alpha increases serum leptin concentrations in humans," Journal of Clinical Endocrinology and Metabolism, vol. 92, No. 9, 1997: 3084-3086.
Kurokawa, Ichiro et al: "New developments in our understanding of acne pathogenesis and treatment," Experimental Dermatology, vol. 18, 2009:821-832.
Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.
Oriuchi, Noboru et al: "Current status of cancer therapy with radiolabeled monoclonal antibody," Annals of Nuclear Medicine, vol. 19, No. 5, 2005:355-365.
Boselli, Joseph et al: Fibronectin: Its relationshp to basement membranes, Light Microscopic Studies, Cell.Res., vol. 5, 1981:391-404.
Hoge, E.A. et al: "Broad spectrum of cytokine abnormalities in panic disorder and posttraumatic stress disorder," Depression and Anxiety, vol. 26, No. 5, May 2009:447-455; Abstract only.

(56) References Cited

OTHER PUBLICATIONS

Mach, Francois: "Toward new therapeutic strategies against neointimal formation in restenosis," Arterioscler Thromb Vasc Biol, vol. 20, 2000:1699-1700.

Morton, Allison, C. et al.: "Interleukin-1 receptor antagonist alters the response to vessel wall injury in a porcine coronary artery model," Cardiovascular Research, vol. 68, 2005: 493-501.

Heyderman, R.S. et al: "Modulation of the endothelial procoagulant response to lipoploysaccharide and tumour necrosis factor-alpha in-vitro: The effects of dexamethasone, pentoxifylline, iloprost and a polyclonal anti-human IL-1 alpha antibody, " Inflamm Res, vol. 44, 1995:275-280.

Joosten, M. et al: "Amelioration of established collagen-induced arthritis (CIA) with anti-IL-1," Agents Actions, vol. 41, Special Conference Issue, 1994:C174-C176.

U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011, 3 pages.

XBiotech, Inc. Pressrelease: "XBiotech Files Investigational New Drug (IND) Application with the FDA for the treatment of Chronic Myelogenous Leukemia," Evaluate, Nov. 22, 2010, 2 pages.

Rhim, JH, et al.: "Cancer cell-derived IL-1 alpha induces Il-8 release in endothelial cells," J Cancer Res Clin Oncol, Jan. 2008, vol. 134(1):45-50. Epub Jul. 11, 2007; (Abstract only).

Sakurai, T. et al.: "Hepatocyte Necrosis Induced by Oxidative Stress and IL-1 alpha Release Mediate Carcinogen-Induced Compensatory Proliferation and Liver Tumorigenesis," Cancer Cell, Aug. 12, 2008, vol. 14:156-165.

Mizutani, H.: "Endogenous neutralizing anti-Il-1 alpha antibodies in inflammatory skin diseases: possible natural inhibitor for over expressed epidermal IL-1," 1999, Journal of Dermatological Science, vol. 20:63-71.

Zhu, Y. et al., "The clinical study about interleukin-1 and tumor necrosis factor alpha in hepatocirrhosis," Chinese Journal of Clinical Hepatology, 2001, vol. 17, Issue 4: 233-234.

Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.

Grahame, V. et al: "The Psychological Correlates of Treatment Efficacy in Acne," Dermatol Psychosom, 2002, vol. 3:119-125.

Murota, H. et al., "Exacerbating factors of itch in atopic dermatitis," Allergology International, 2017, No. 66:8-13.

Fenini, G. et al., "Potential of IL-1, IL-18 and Inflammasome Inhibition for the Treatment of Inflammatory Skin Diseases," Frontiers in Pharmacology, May 2017, vol. 8:1-20.

Carrasco, Daniel et al: "An Open Label, Phase 2 Study of MABp1 Monotherapy for the Treatment of Acne Vulgaris and Psychiatric Comorbidity," Journal of Drugs in Dermatology, Jun. 2015, vol. 14, Issue 6: 560-564.

Rubinow, David R. et al: "Reduce anxiety and depression in cystic acne patients after successful treatment with oral isotretinoin," Journal of the American Academy of Dermatology, 1987, vol. 17, No. 1:25-32.

Kaymak, Yesim et al: "Comparison of depression, anxiety and life quality in acne vulgaris patients who were treated with either isotretinoin or topical agents, The International Society of Dermatology," 2009, vol. 48:41-46.

Dinarello, Charles A. et al: "Treating inflammation by blocking interleukin-1 in a broad spectrum of diseases," Nature Reviews/Drug Discovery, Aug. 2012, vol. 11: 633-652.

Rossi, Silvia et al.: "Interleukin-1 beta causes anxiety by interacting with the endocannabinoid system," The Journal of Nleuroscience, Oct. 3, 2012, vol. 32, No. 40:13896-13905.

Szabo, K. et al: "lnterleukin-1 A +4845(G>T) polymorphism is a factor predisposing to acne vulgaris," Tissue Antigens, 2010, vol. 76:411-415.

Bonifati, C. et al.: "IL-lalpha, IL-1 beta and psoriasis: conflicting results in the literature. Opposite behaviour of the two cytokines in lesional or non-lesional extracts of whole skin," Journal of Biological Regulators and Homeostatic Agents, Oct. 1997, vol. 11, No. 4:133-136.

Gonzalez-Lopez, M.A. et al: "New-onset psoriasis following treatment with the interleukin-1 receptor antagonist anakinra," British Journal of Dermatology, May 2008, vol. 158, No. 5:1146-1148.

Yost, J. and J.E. Gudjonsson: "The role of TNF inhibitors in psoriasis therapy: new implications for associated comorbidities," Medicine Reports, May 2009, vol. 1, No. 30:1-4.

Kanni, Theodora, et al.: "MABp1 Targeting IL-1 alpha for moderate to severe hidradenitis suppurativa not eligible for adalimumab: A randomized study," Journal of Investigative Dermatology, 2018, vol. 138:795-801.

Riis, Peter Theut et al.: "Investigational drugs in clinical trials for hidradenitis suppurativa," Expert Opinion on Investigational Drugs, 2018, vol. 27, No. 1:43-53.

Rectenwald et al., "Direct Evidence for Cytokine Involvement in Neointimal Hyperplasia,"; Circulation, vol. 102, pp. 1697-1702, Oct. 3, 2000.

Kamari et al., BBRC: 405,pp. 197-203 (Year: 2011), 7 pages.

Waehreetal., Circulation: 109, pp. 1966-1972 (Year: 2004).

Moyeretal., Am. J. Pathol.:138, pp. 951-960 (Year: 1991).

Larionov et al., Acta Neuropathol: 113, pp. 33-43 (Year: 2007).

Zaragoza et al. (2011), J. of Biomedicine and Biotechnology, vol. 2011, p. 1-13.

Patti et al., AM. J. Cardiol: 89., pp. 372-376 (Year: 2002).

Beasley, Debbie and Angela L. Cooper: "Constitutive expression of interleukin-1 alpha precursor promotes human vascular smooth muscle cell proliferation," American Physiological Society, 1999, No. 276:H901-H912.

Morton et al. Crdiovascular Research, vol. 68, pp. 401-501 (Year: 2005).

Xbiotch IND for the treatment of Chronic Myelogenous Leukemia, pp. 1 (Year: 2010).

Mandinov, L. et al.: "Inhibition of in-stent restenosis by oral copper chelation in porcine coronary arteries," Am J Physiol Heart Circ Physiol, 2006, vol. 291:H2692-H2697.

Giamarellos-Bourboulis, EvangelosJ. MABpi in Hidradenitis Suppurativa Refractory to Adalimumab, ClinicalTrials.gov, Identifier: NCT02643654, 19 pages (Dec. 31, 2015). (Year: 2015).

Kimball et al. Assessing the validity, responsiveness and meaningfulness of the Hidradenitis Suppurativa Clinical Response (HiSCR) as the clinical endpoint for hidradenitis suppurativa treatment. British Journal of Dermatology vol. 171:1434-1442 (2014). (Year: 2014).

Martin-Ezquerra et al. Use of biological treatments in patients with hidradenitis suppurativa. Giornale Italiano di Dermatologia e Venereologia. Journal on Dermatology and Sexually Transmitted Diseases. vol. 152(4):373-8, Aug. 2017. Article first published online Dec. 16, 2016. (Year: 2017).

Kelekis, N.L et al., "Ultrasound aids and diagnosis and severity assessment of hidradenitis suppurativa", British Journal of Dermatology, 2010, vol. 162, Issue 6, pp. 1395-1416.

International Search Report issued in corresponding international patent application No. PCT/IB2018/000209 dated Jul. 5, 2018; 4 pages.

Immunobiology, Janeway et al., The immune system in health and disease, 3rd edition, 1997section 3.4 and figure 3.4, 9 pages.

Fujii, Masakazu et al.: "A case of advanced gastric cancer with carcinomatous ascites successfully treated with intraperitoneal administration of CDDP and TS-1," Japanese Journal of Gastoenterological Surgery, 2006, vol. 39:189-195.

Wang et al. Nuc. Acids Res. 1999, vol. 27, pp. 4609-4618.

Kaufman et al Blood, 1999, vol. 94, pp. 3178-3184.

Wigley et al. Reprod Fed Dev, 1994, vol. 6, pp. 585-588.

Campbell et al. Theriology, 1997, vol. 47, No. 1, pp. 63-72.

Kishore et al, Immunopharmacology, 2000, vol. 49, pp. 159-170.

Li et al, Cancer Research, 2002, vol. 62, pp. 417-423.

Eugui et al. (1990) PNAS 87: 1305-1309.

GE Healthcare Instructions, 2005, 12 pages.

(56) References Cited

OTHER PUBLICATIONS

Kaji, M.: "E-selectin expression induced by pancreas-carcinoma-derived interleukin-1alpha results in enhanced adhesion of pancreas-carcinoma cells to endothelial cells," Mar. 1996, vol. 60Issue 5:712-717(Abstract).
Schlitt, Axel et al., CD14+D16+ monocytes in coronary artery disease and their relationship to serum TNF-alpha levels, Thromb Haemost, 2004, vol. 92:419-424.
Ziegler-Heitbrock, Loems, The CD14+CD16+ blood monocytes: their role in infection and inflammation, Journal of Leukocyte Biology, Mar. 2007, vol. 81:584-592.
Beige, Kai-Uwe et al., The Proinflammatory CD14+ CD16+DR++ Monocytes Are a Major Source of TNF1, The Journal of Immunology, 2002, vol. 168:3536-3542.
Iwahashi, Mitsuhiro et al., Expression of Toll-Like Receptor 2 on CD16+ Blood Monocytes and Synovial Tissue Macrophages in Rheumatoid Arthritis, Arthritis and Rheumatism, 2004, vol. 50, No. 5:1457-1467.
Ulrich, C. et al., Proinflammatory CD14+CD16+ Monocytes are Associated with Subclinical Atherosclerosis in Renal Transplant Patients, American Journal of Transplantation, 2008, vol. 8:103-110.
Heine, GH., et al., CD14++CD16+ monocytes but not total monocyte numbers predict cardiovascular events in dialysis patients, Kidney International, 2008, vol. 73:622-629.
Joosten, Leo A.B. et al: "Anticytokine Treatment of Established Type II Collagen-Induced Arthritis in DBA/1 Mice," Arthritis & Rheumatism, May 1996, vol. 39, No. 5:797-809.
Huey-Huey Chua et al., Regulation of IAPs Gene Family by Interleukin-1 a and Epstein-Barr Virus in Nasopharyngeal Carcinoma, Head & Neck 30, No. 12 (2008): 1575-85.
Yoichi Matsuo et al., IL-1a Secreted by Colon Cancer Cells Enhances Angiogenesis: The Relationship between IL-1 a Release and Tumor Dells' Potential for Liver Metastasis, Journal of Surgical Oncology 99, No. 6 (2009): 361-67.
Ron N. Apte et al., The Involvement of IL-1 in Tumorigenesis, Tumor Invasiveness, Metastasis and Tumor-Host Interactions, Cancer and Metastasis Reviews 25, No. 3 (Sep. 1, 2006): 387-408.
Tumor Metastasis, chiefly-edited by Liao Zijun, p. 59, Shaanxi Science & Technology Press, Feb. 28, 2007, 1 page.
Chang, Cheng-Hsien et al.: "Interleukin-1 alpha Released from Epithelial Cells after Adenovirus Type 37 Infection Activates Intercellular Adhesion Molecule 1 Expression on Human Vascular Endothelial Cells," Journal of Virology, 2002:427-431.
Orjalo, Arturo V. et al.: "Cell surface-bound IL-1 alpha is an upstream regulator of the senescence-associated IL-6/ IL-8 cytokine network," PNAS, 2009, vol. 106, No. 40:17031-17036.
Pazzaglia, Laura et al: "Activation of Metalloproteinases-2 and -9 by Interleukin-1 alpha in S100A4-positive Liposarcoma Cell Line: Correlation with Cell Invasiveness," Anticancer Research, 2004, vol. 24:967-972.
Saitta, P. et al: "An Update on the Presence of Psychiatric Comorbidities in Acne Patients, Part 2: Depression, Anxiety, and Suicide," CUTIS, Aug. 2011, vol. 88:92-97.
Marques-Deak, Andrea et al: "Measurement of cytokines in sweat patches and plasma in healthy women: Validation in a controlled study," Journal of Immunological Methods, vol. 315, 2006: 99-109.
Clinical Trial Review: "Acne," Journal of Drugs in Dermatology (JD online Today), Jun. 2012, vol. 11, Issue 6:1-3; <<http://jddonline.eom/articles/dermatology/S1545961612P0780X/1>>, last visited on Jan. 17, 2017.
Yamada, Takayuki et al.: "Growth Dependency of a new human pancreatic cancer cell line, YAPC, on autocrine interleukin-1 alpha stimulation," Int. J. Cancer, 1998, vol. 76:141-147.
El-Osta, Hazem et al.: "Successful treatment of Castleman's Disease with Interleukin-1 receptor antagonist (Anakinra)," Molecular Cancer Therapy, 2010, vol. 9:1485-1488.
Clinical Trial Review: Acne; <<http://jddonline.eom/articles/dermatology/S1545961612P0780X/1>>, last visited on Oct. 16, 2014; 3 pages.
Stark et al., British Journal of Cancer, 83(10):1261-1267, 2000.
Feldman et al., American Family Physician, 69(9):2123-30, 2004.
Oldenburg, H.S.A., et al. Cachexia and the acute-phase protein response in inflammation are regulated by interleukin-6. Eur. J. Immunol., 1993, vol. 23, p. 1889-1894.
Hong, David S. et al: "MABp1, a first-in-class true human antibody targeting interleukin-1alpha in refractory cancers: an open-label, phase 1 dose-escalation and expansion study," Lancet Oncol, 2014, vol. 15:656-66.
Fong Y; Moldawer L L; Marano M; Wei H; Barber A; Manogue K; Tracey K J; Kuo G; Fischman D A; Cerami A; et al., "Cachectin/TNF or IL-1 alpha induces cachexia with redistribution of body proteins.", American Journal of Physiology, American Physiological Society, US, US, (19890301), vol. 256, No. 3, ISSN 0002-9513, pages R659-R665, XP009184008.
Hong, David S. et al.: "Abstract A211: A phase I study of MABp1, a first-in-human, first-true human monoclonal antibody against the Il-1 in patients with advanced cancer," Molecular Cancer Therapeutics, 2011, (1 page).
Kumar, Suresh, et al: "Interleukin-1 alpha promotes tumor growth and cachexia in MCF-7 xenograft model of breast cancer," American Journal of Pathology, 2003, vol. 163:2531-2541.
Ma, Joseph D et al: "Novel investigational biologies for the treatment of cancer cachexia," Expert Opin. Biol. Ther., 2014, vol. 14(8):1113-1120.
Madeddu, Clelia and Mantovani, Giovanni: "An update on promising agents for the treatment of cancer cachexia," Current Opinion in Supportive and Palliative Care, 2009, vol. 3:258-262.
Simard, John: "Early Results from XBiotech's Clinical Study in Cachexia Hint at Breakthrough Treatment," XBiotech News: Clinical Study in Cachex . . . , 2011, (3 pages), (retrieved from the Internet <http://www.xbiotech.com/about/news/early-results-from-xBiotechs-clinical-study-in-cachexia.html>, last visited on Jul. 22, 2015.
Tamura, Sumie et al: "Involvement of human interleukin 6 in experimental cachexia induced by a human uterine cervical carcinoma xenograft," Clinical Cancer Research, Nov. 1995, vol. 1:1353-1358.
Sturlan, Sanda, et al: "In vivo gene transfer of murine interleukin-4 inhibits colon-26-mediated cancer cachexia in mice," Anticancer Research, 2002, vol. 22:2547-2554.
Costelli, Paola et al: "Interleukin-1 receptor antagonist (IL-1ra) is unable to reverse cachexia in rats bearing an ascites hepatoma (Yoshida AH-130)," Cancer Letters 95, 1995, pp. 33-38.
Larsen C.M. et al. Interleukin-1-receptor antagonist is type 2 diabetes mellitus. New England Journal of Medicine, 2007, vol. 356, p. 1517-1526.
Larsen, C.M., et al. Sustained effects of interleukin-1 receptor antagonist treatment in type 2 diabetes. Diabetes Care, 2009, vol. 32, p. 1663-1668.
Levetan, C. Oral antidiabetic agents in type 2 diabetes. Current Medical Research and Opinion, 2007, vol. 23, No. 4, p. 945-952.
Van Asseldonk, E.J.P., et al. One week treatment with the IL-1 receptor antagonist anakinra leads to a sustained improvement in insulin sensitivity in insulin resistant patients with type 1 diabetes mellitus. Clinical Immunology, 2015, vol. 160, p. 155-162.
Tzanetakou, V. et al., "Safety and Efficacy of Anakinra in Severe Hidradenitis Suppurativa: A Randomized Clinical Trial", Jama Dermatology, (20160100), vol. 152, No. 1, doi:10.1001/jamadermatol.2015.3903, ISSN 2168-6068, pp. 52-59, XP055617164.
Kanni, T. et al., "MABpI Targeting IL-1a for Moderate to Severe Hidradenitis Suppurativa Not Eligible for Adalimumab: A Randomized Study", Journal of Investigative Dermatology, (20171110), vol. 138, No. 4, ISSN 1523-1747, pp. 795-801, XP055532244.
Genbank, (May 19, 2005), Database accession No. AY510107.1, XP008146519.
Francois Mach., "Toward New Therapeutic Strategies Against Neointimal Formation in Restenosis", Arterioscler Thromb Vasc Biol, (2000), vol. 20, pp. 1699-1700, XP055244035.
Eisenhauer et al., Eur J Cancer. Jan. 2009;45(2):228-47.
Haller, M. "Converting Intravenous Dosing to Subcutaneous Dosing with Recombinant Human Hyaluronidase", Pharmaceutical Technology, Oct. 2, 2007, vol. 31, Issue 10 (Year: 2007).

(56) References Cited

OTHER PUBLICATIONS

Schmidt, R. "Dose-Finding Studies in Clinical Drug Development"; EurJ Clin Pharmacol (1988) 34:15-19. (Year: 1988).
Walpole et al. "The weight of nations: an estimation of adult human biomass"; BMC Public Health 2012, 12:439. (Year: 2012).
A.C. Morton, et al., "Investigation of IL-1 Inhibition in Patients Presenting with Non-St Elevation Myocardial Infarction Acute Coronary Syndroms (The MRC ILA Heart Study)," Heart, vol. 97, Suppl 1., Jun. 2011.
Lapins et al., "Coagulase-negative staphylococci are the most common bacteria found in cultures from the deep portions of hidradenitis suppurativa lesions, as obtained by carbon dioxide laser surgery". British Journal of Dermatology. 1999; 140: 90-95.
Morton, Allison C., et al., "The effect of interleukin-1 receptor antagonist therapy on markers of inflammation in non-ST elevation acute coronary syndromes: the MRC-ILA Heart Study," European Heart Journal, vol. 36, pp. 377-384 (2015).
Clinical trial: NCT02643654, "MABp1 In Hidradenitis Suppurativa Refractory to Adalimumab", Oct. 9, 2016 (Oct. 9, 2016), Retrieved from the Internet: URL: https://https://clinicaltrials.gov/ct2/show/NCT02643654. (10 pages).
Hessam, et al., "Microbial Profile and Antimicrobial Susceptibility of Bacteria Found in Inflammatory Hidradenitis Suppurativa Lesions," Skin Pharmacol Physiol 2016; 29:161-167.
Schultz, et al., "Endogenous interleukin-1α promotes a proliferative and proinflammatory phenotype in human vascular smooth muscle cells," Am J Physiol Heart Circ Physiol, Jun. 2007; 292(6): H2927-34.
NCT01270945—Safety and Preliminary Efficacy Study of an Anti inflammatory Therapeutic Antibody in Reducing Restenosis (version 6; submitted May 15, 2012). (8 pages).
Wei et al, "Clinical key techniques of routine operation in cardiac diagnosis and treatment", Science and Technology Literature Press, 1st edition—"Restenosis and related factors", p. 239, publication date: May 2009. Chinese-language publication. English translation of relevant excerpt attached. (1 page).
Peigang et al., "Theory and Practice of Neurosurgical Diseases", Tianjin Science and Technology Press, 1st edition—Complications and Countermeasures of Stent Implantation, p. 123, publication date: Oct. 2011. Chinese-language publication. English translation of relevant excerpt attached. (1 page).
Chamberlain, Janet et al., "Interleukin-1B and signaling of Interleukin-1 in Vascular Wall and Circulating Cells Modulates the Extend of Neointima Formation in Mice," American Journal of Pathology, vol. 168, No. 4, pp. 1396-1403, Apr. 2006.
Sun Qinguo et al., "Coronary Heart Disease", chiefly edited by China Medical Science and Technology Press, 1st edition, "Interventional Therapy of Coronary Heart Disease", pp. 203-208, publication date: Jan. 2010. Chinese-language publication. English translation of relevant excerpt attached. (1 page).
Rishi et al., "Hospital anxiety and depression scale assessment of 100 patients before and after using low vision care: A prospective study in a teriary eye-care setting," Indian J Ophthalmol. Nov. 2017; 65(11): 1203-1208.
Westhuis et al., "Development and Validation of the Clinical Anxiety Scale: A Rapid Assessment Instrument for Empirical Practice," Educational and Psychological Measurement, 49:153-163, 1989.
Snaith, R.P. The Hospital Anxiety and Depression Scale. Health Qual Life Outcomes 1, 29 (2003). (4 pages).
Ramli et al., "Acne analysis, grading and computational assessment methods: an overview," Skin Research and Technology 2012; 18:1-14.
Mennin et al., "Screening for social anxiety disorder in the clinical settin: using the Liebowitz Social Anxiety Scale," Anxiety Disorders, 16:661-673, 2002.
Radke et al., "Outcome after treatment of coronary in-stent restenosis results from a systematic review using meta-analysis techniques," European Hear Journal, vol. 24, No. 3, pp. 266-273, Feb. 1, 2003.
Janik, John E., "Phase II Trial of Interleukin 1a and Indomethacin in Treatment of Metastatic Melanoma,"Journal of the National Cancer Institute, vol. 88, No. 1, pp. 44-49, Jan. 3, 1996.
US National Institutes of Health, "Anakinra With or Without Dexamethasone in Treating Patients with Smoldering or Indolent Mutiple Myeloma," ClinialTrials.gov, US, (Mar. 12, 2008), pp. 1-4, URL: http://clincaltrials.gov/ct2/show/NCT00635154.
"Clinical key techniques of routine operation in cardiac diagnosis and treatment", chiefly edited by Wu Wei et al., Science and Technology Literature Press, 1st edition—"Restenosis and related factors", p. 239, publication date: May 2009 ["Evidence 1"].
"Theory and Practice of Neurosurgical Diseases", chiefly edited by Lu Peigang et al., Tianjin Science and Technology Press, 1st edition—Complications and Countermeasures of Stent Implantation, p. 123, publication date: Oct. 2011 ["Evidence 2"].
"Coronary Heart Disease", chiefly edited by Sun Qinguo et al., China Medical Science and Technology Press, 1st edition, "Interventional Therapy of Coronary Heart Disease", pp. 203-208, publication date: Jan. 2010 ["Evidence 3"].
Ofran, Yanay, et al., "Automated Identification of Complementarity Determining Regions (CDRs) Reveals Peculiar Characteristics of CDRs and B Cell Epitopes," The Journal of Immunology, vol. 181, pp. 6230-6235, (2008).

\* cited by examiner

| Time (days) | Sample | Injected MABP1 conc. in Blood (mg) | Observed Mean MABP1 conc. in Plasma (ug/ml) | Std. Dev. In Observed MABP1 conc. in Plasma (ug/ml) |
|---|---|---|---|---|
| 0 | RD019U | 0 | 0.0 | 0.0 |
| 1 | RD019S-1 | 110 | 3.2 | 0.6 |
| 7 | RD019S-2 | 0 | 7.0 | 0.3 |
| 14 | RD019S-3 | 110 | 5.8 | 0.7 |
| 35 | RD019S-4 | 0 | 1.4 | 0.2 |

ARTHRITIS TREATMENT

CROSS-REFERENCE TO RELATED APPLICATIONS

This application is a continuation application of U.S. patent application Ser. No. 15/235,263 filed on Aug. 12, 2016, which is a continuation application of U.S. patent application Ser. No. 13/162,705 filed on Jun. 17, 2011 (now abandoned), which claims priority from U.S. provisional patent application Ser. No. 61/356,176 filed on Jun. 18, 2010. All patent applications are incorporated herein by reference in their entirety.

STATEMENT AS TO FEDERALLY SPONSORED RESEARCH

Not applicable.

FIELD OF THE INVENTION

The invention relates generally to the fields of immunology, inflammation, arthritis, and medicine. More particularly, the invention relates to the use of antibodies (Abs) which specifically bind interleukin-1α (IL-1α) to treat one or more symptoms of arthritis.

BACKGROUND

Arthritis, the most common cause of disability in the United States, is a collection of different conditions such as osteoarthritis, rheumatoid arthritis, gout, psoriatic arthritis, septic arthritis, and reactive arthritis. All types of arthritis are characterized by joint inflammation which causes pain, swelling, redness, stiffness, and warmth at that affected site. Because afflicted subjects are less mobile due to pain and stiffness, arthritis can indirectly lead to obesity, high cholesterol, and/or heart disease. Arthritis can also cause extraarticular disease such as iritis, uveitis, oral ulcers, inflammation of the gastrointestinal tract, inflammation of the genitourinary tract, and skin lesions.

For most types of arthritis, no cure exists and treatment is largely symptomatic, e.g., administration of analgesics and anti-inflammatory drugs. Non-steroidal anti-inflammatory drugs (NSAIDs) can be used to reduce inflammation and pain. While generally effective, NSAIDs may cause side effects such as abdominal pain, bleeding, ulcers, and liver and kidney damage. Corticosteroids are effective at reducing inflammation and joint damage, but can cause a number of side effect are also associated including bruising, weight gain, cataracts, bone thinning, diabetes, and hypertension. Other drugs commonly used to treat arthritis are methotrexate, cyclosporine, cyclophosphamide, leflunomide, hydroxychloroquine, sulfasalazine, and minocycline. These too can cause side effects such as liver damage and immunosuppression. Tumor necrosis factor (TNF) inhibitors like etanercept (Enbrel), infliximab (Remicade), and adalimumab (Humira) are also useful for treating arthritis. Side effects of TNF inhibitors include injection site reactions, heart failure, lymphoma, and increased risk of infection.

SUMMARY

The invention is based on the discovery that administration of an antibody (Ab) that specifically targets IL-1α in a human subject suffering from arthritis reduces the number of CD14+IL-1α+ peripheral blood monocytes in the subject and markedly ameliorates inflammation in both articular and extraarticular sites—all without any observed side effects other than pain at the administration site.

Accordingly, the invention features a method of treating an inflammatory pathology associated with arthritis in a human subject by administering to the subject a pharmaceutical composition including a pharmaceutically acceptable carrier and an amount of an anti-IL-1α antibody effective to reduce at least one symptom of the inflammatory pathology in the subject. The symptom can be joint inflammation such as of the wrist or shoulder, or inflammation of the eye such as uveitis. The anti-IL-1α antibody can be a monoclonal antibody such as an IgG1. The anti-IL-1α antibody can be the monoclonal antibody designated as MABp1 or a monoclonal antibody that includes one or more complementarity determining regions (CDRs) of MABp1.

The pharmaceutical composition can be administered to the subject by injection, subcutaneously, intravenously, intramuscularly, intraocularly, or directly into an inflamed joint. The antibody might also be administered to the eye topically. In the method, the amount of the anti-IL-1α antibody effective to reduce at least one symptom of the inflammatory pathology in the subject can be sufficient to raise the subject's peripheral blood concentration of anti-IL-1α antibody to at least 4 ug/ml; and/or sufficient to decrease the number of the subject's CD14+IL-1α+ peripheral blood monocytes by at least 5%.

The method might also include a step of measuring the number of CD14+IL-1α+ monocytes in the subject's peripheral blood after administration of the pharmaceutical composition, e.g., wherein the step of measuring the number of CD14+IL-1α+ monocytes in the subject's peripheral blood is performed at least two different time points after administration of the pharmaceutical composition.

In another aspect, the invention features a method inducing monocyte vacuolization in a subject by administering to the subject a pharmaceutical composition including a pharmaceutically acceptable carrier and an amount of an anti-IL-1α antibody effective to induce vacuole formation in monocytes.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27$^{th}$ Edition, Lippincott, Williams & Wilkins, 2000.

As used herein, an "antibody" or "Ab" is an immunoglobulin (Ig), a solution of identical or heterogeneous Igs, or a mixture of Igs. An "antibody" can also refer to fragments and engineered versions of Igs such as Fab, Fab', and F(ab')2 fragments; and scFv's, heteroconjugate Abs, and similar artificial molecules that employ Ig-derived CDRs to impart antigen specificity. A "monoclonal antibody" or "mAb" is an Ab expressed by one clonal B cell line or a population of Ab molecules that contains only one species of an antigen binding site capable of immunoreacting with a particular epitope of a particular antigen. A "polyclonal antibody" or "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule.

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses compositions and methods for treating a symptom or pathologic process associated with arthritis in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein. Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, $49^{th}$ Edition, McGraw-Hill Medical, 2010; and Fauci et al., Harrison's Principles of Internal Medicine, $17^{th}$ Edition, McGraw-Hill Professional, 2008

Treatment of Arthritis Symptoms

The compositions and methods described herein are useful for treating an inflammatory pathology associated with arthritis in a mammalian subject by administering to the subject a pharmaceutical composition including an amount of an anti-IL-1α antibody effective to reduce at least one symptom of the inflammatory pathology in the subject. The mammalian subject might be any that suffers from arthritis including, human beings, dogs, cats, horses, cattle, sheep, goats, and pigs. Human subjects might be male, female, adults, children, seniors (65 and older), and those with other diseases. The particular symptom or pathologic process associated with arthritis can be inflammation, pain, stiffness, or degeneration of a joint (e.g., in the wrist, digits [metacarpal or metatarsal joints], elbows, shoulders, hips, knees, ankles, foot, neck, or back) or extraarticular tissue (e.g., iritis, uveitis, oral ulcers, inflammation of the gastrointestinal tract, inflammation of the genitourinary tract, or skin lesions).

Antibodies and Other Agents that Target IL-1α

Any suitable type of Ab that specifically binds IL-1a and reduces a symptom or pathologic process caused by arthritis in a subject might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1 \times 10^9$ $M^{-1}$ or greater (e.g., greater than $9 \times 10^{10} M^{-1}$, $8 \times 10^{10}$ $M^{-1}$, $7 \times 10^{10}$ $M^{-1}$, $6 \times 10^{10}$ $M^{-1}$, $5 \times 10^{10}$ $M^{-1}$, $4 \times 10^{10}$ $M^{-1}$, $3 \times 10^{10}$ $M^{-1}$, $2 \times 10^{10}$ $M^{-1}$, or $1 \times 10^{10}$ $M^{-1}$). In a preferred embodiment, the invention utilizes a fully human mAb that includes (i) an antigen-binding variable region that exhibits very high binding affinity for human IL-1α and (ii) a constant region that is effective at both activating the complement system though C1q binding and binding to several different Fc receptors. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 monoclonal antibody described in U.S. patent application Ser. No. 12/455,458 filed on Jun. 1, 2009. Other useful mAbs are those that include at least one but preferably all the CDRs of MABp1.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, Monoclonal Abs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and E. coli cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, monoclonal Abs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the human IL-1α mAbs might be conjugated another molecule such as a cytotoxin. A human IL-1α specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, and $^{211}At$), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), Pseudomonas exotoxin (PE) A, PE40, abrin, saporin, pokeweed viral protein, ethidium bromide, glucocorticoid, anthrax toxin and others. See, e.g., U.S. Pat. No. 5,932,188.

While the IL-1α specific Abs described above are preferred for use the invention, in some cases, other agents that specifically target IL-1α might be used so long as their administration leads to improvement of one or more symptoms of arthritis. These other agents might include small organic molecules, aptamers, peptides, and proteins that specifically bind IL-1α.

Pharmaceutical Compositions and Methods

The anti-IL-1α Ab compositions may be administered to animals or humans in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent).

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., an inflamed joint, or the uvea or conjuctiva) by, for example, injection or topical application. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in arthritis patients as measured by the improvement in pain and function as well as the prevention of structural damage. As is well known in the medical arts, dosage for any one animal or human depends on many factors, including the subject's size, body surface area, age, the particular composition to be administered, sex, time and route of administration, general health, and other drugs being administered concurrently. A preferred dose is one that is sufficient to raise the subject's peripheral blood concentration of anti-IL-1α Ab to at least 4 (e.g., at least 4, 5, 6, 7, 8, 9, 10, 20, 30, 40, 50, 100, 200, 300, 400, 500, 1000, 2500, or 5000) micrograms/ml. It is expected that an appropriate dosage of Abs would be in the range of about 0.2 to 20 (e.g., 0.5, 1, 2, 3, 4, 5, 6, 7, 8, 9, 10, 15, 20, 30, 50, or 100) mg/kg body weight for subcutaneous administration and about 0.001 to 50 (e.g., 0.001, 0.01, 1, 5, 10, 15, 25, or 50) mg per eye for topical administration to the eye. The dose may be given repeatedly, e.g., hourly, daily, weekly, or monthly.

EXAMPLES

Example 1—Xilonix™

Xilonix™ is a sterile injectable liquid formulation of 15 mg/mL MABp1 in a stabilizing isotonic buffer (pH 6.4). Each 10-mL Type I borosilicate glass serum vial contains 5 mL of the formulation, and is sealed with a 20-mm Daikyo Flurotec butyl rubber stopper and flip-off aluminum seal. The product is stored at 5±3° C., with excursions to room temperature permitted. The exact composition of the drug product is shown below:

| Composition of the Drug Product (Xilonix ™) | | | |
|---|---|---|---|
| Ingredient | Grade | Manufacturer | Concentration |
| MABp1 antibody | GMP | XBiotech | 15 mg/mL |
| sodium phosphate dibasic | compendial | J T Baker | 12 mg/mL |
| citric acid monohydrate | compendial | J T Baker | 2 mg/mL |
| Trehalose•2H2O (high-purity low endotoxin) | compendial | Ferro-Pfanstiehl | 60 mg/mL |
| polysorbate 80 | compendial | J T Baker | 0.2 mg/mL |
| Phosphoric acid, to adjust pH | compendial | J T Baker | 0.04 mg/mL |
| water for injection | compendial | Microbix | q.s. |

Example 2—Treatment of Reactive Arthritis with an IL-1α-Specific Monoclonal Antibody A 48 year-old male patient with reactive arthritis was administered a total 220 milligrams of MABp1, an IL-1α-specific monoclonal antibody described in U.S. patent application Ser. No. 12/455,458 filed on Jun. 1, 2009. The patient had a long history of reactive arthritis, starting at age 16, when he was diagnosed with Reiter's syndrome during hospitalization for severe inflammation in his left knee. This inflammation resolved, yet the patient experienced periodic relapses in several joints until his mid-twenties. No further episodes occurred until, at age 35, the patient had a severe unilateral episode of uveitis that lasted for 8 weeks. The uveitis was poorly managed with ophthalmic corticosteroids and oral NSAIDS, resulting in some scaring. The patient subsequently experienced at least three additional episodes of uveitis of varying intensities, one episode requiring subcorneal injection of corticosteroids.

Just prior to his 48$^{th}$ birthday, the patient developed severe pain in his left shoulder and wrist. Evident swelling and redness with almost complete loss of mobility affected the wrist. The patient was unable to abduct his left arm greater than about 20° due to intense shoulder pain. On that day, the patient was given a subacromial injection of corticosteroids into the left shoulder. The patient reported that the condition continued to worsen with pain from shoulder and wrist reportedly becoming continuous, interrupting work and preventing sleep. In addition, pain and irritation in the left eye ensued, indicating onset of an episode of uveitis. This was reportedly the first time joint inflammation and uveitis occurred together. The patient was taking ophthalmic corticosteroids, oral and topical ophthalmic NSAIDS with little apparent benefit.

On day 0 (forty-two days after the subacromial injection of corticosteroids), the patient was administered four subcutaneous injections of MABp1, delivering a total of 110 mg of MABp1 (in equal doses). No side effects other than pain during injection was reported. Blood was drawn by venous puncture immediately prior to injection into two 5 ml sodium heparin tubes. Plasma analysis using an enzyme-linked immunadsorbant assay (ELISA) for the detection of existing endogenous anti-IL-1α antibodies revealed no pre-existing antibodies.

On day 1, the patient reported that he woke up that morning without the throbbing pain that had become the "first sensation upon waking." Over the next several days there was an evident improvement in mobility. There was no induration or redness at the injection sites. A blood draw was taken and flow cytometric analysis (FACS) was performed to evaluate leuckocyte subsets and IL-1α expression on monocytes. Analysis was also performed on plasma to determine levels of MABp1 and to begin collection of pharmacokinetic (pK) data for MABp1. FACS analysis of PBMC revealed that most CD14+ monocytes (72.6%) expressed IL-1α. A MABp1 plasma concentration of 3.2 μg/ml was observed.

On day 6, another blood sample was taken and analyzed using FACS and for MABp1. The frequency of CD14+ monocytes stained by MABp1 had declined to 47.3%. Plasma levels of MABp1 had increased to 7 μg/ml. Although not confirmed, the increase in MABp1 concentration was considered to reflect a depot effect of the subcutaneous administration of MABp1. Although there had been improvement, the patient still exhibited considerable tenderness and pain with movement and the uveitis had flared since the previous weekend, where the patient had attended a party and consumed alcohol. The patient was administered another 110 mg of MABp1 subcutaneously.

On day 14, a blood sample was taken and analyzed using FACS and pK analysis was performed on plasma. CD14+ monocyte frequency stained by MABp1 further declined to 21.7%. However, plasma levels of MABp1 had also declined to 5.8 μg/ml. This was unanticipated, since plasma levels of MABp1 had increased over the week after the first injection.

Approximately one month after the first injection of MABp1 the patient was reevaluated. Marked improvement was noted in mobility and there was no pain in the wrist. Pain in shoulder was present only upon abduction to 90°. FACS analysis revealed no detectable CD14+ monocytes stained by MABp1. Plasma levels of MABp1 had declined to 1.6 μg/ml, suggesting a half-life for MABp1 of about two weeks.

Over the course of the next several weeks the patient showed gradual but continuous improvement in mobility. There was complete resolution of the uveitis. The improvement was noted even though the patient discontinued use of all medications after the first injection of MABp1. Approximately three months after the first injection of MABp1, the frequency of CD14+ monocytes stained by MABp1 had returned to pre-treatment levels. MABp1 levels in plasma declined to 0.07 μg/ml. However, the patient continued to do well with continuing improvement in mobility of the shoulder.

Example 3—Screening of Plasma Samples for Endogenous Autoantibody Against hIL-1A and Pharmacokinetics of MABp1

A method was developed for the screening of plasma samples for endogenous autoantibody against human IL-1α (hIL-1α) using a direct ELISA. This method was also used to determine pharmacokinetics (pK) of MABp1 after administration, with the exception, that higher dilutions plasma samples were made.

The direct ELISA involves coating of recombinant human IL-1α on a polystyrene microplate. The bound human IL-1A captures endogenous anti-human IL-1α antibody from test samples. An HRP-conjugated-Fc specific, mouse-anti-human IgG is then used to detect the captured endogenous anti-human IL-1A antibody, followed by treatment with TMB substrate. On reacting with HRP enzyme, the TMB substrate produces a deep blue-colored soluble product. The enzymatic reaction is stopped by the addition of a stop solution that turns the blue-colored product to yellow. The colorimetric measurements are carried out on a microplate reader at 450 nm.

About 5 ml plasma sample per sample is provided. Plasma is kept at 2-8° C. prior to aliquoting and storage at −80° C. Plasma samples are diluted 1:500, 1:1000 and 1:2000-fold to use as samples. A positive control in buffer is used containing 20 μg/ml MABp1 antibody stock as 1:5,000 and 1:10,000-fold dilutions on microplate. Buffer is used as a negative control as well as a pre-determined negative control plasma, which is diluted as 1:1,000, 1:2,000 and 1:5,000. An additional positive plasma control is used, which is plasma spiked with 20 μg/ml MABp1 antibody and diluted as 1:5,000 and 1:10,000 for samples on the microplate.

Figure 1:
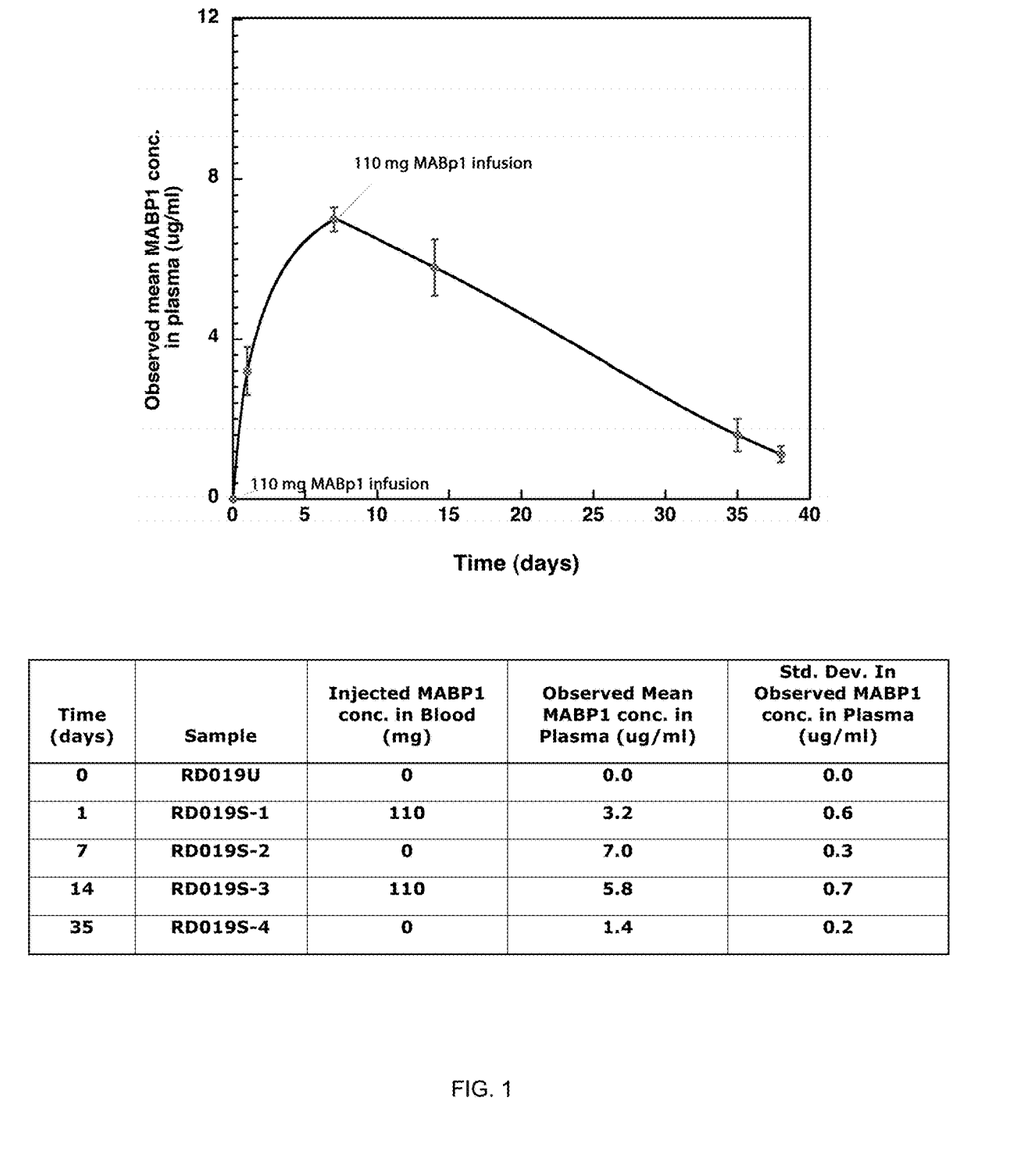
FIG. 1 is a graph and table showing the pharmacokinetics of MABp1 after administration to a human subject with reactive arthritis.

If the positive control value falls within ±2 standard deviation, the ELISA data is considered acceptable. However if the QC positive control value falls beyond ±2 standard deviation, the ELISA data is considered unacceptable and the experiment would be repeated. Using a Kaleidagraph, the logarithmic mean absorbance of standard solution is plotted as a function of logarithmic concentration along with absorbance error bars. The standard curve should exhibit a linear behavior. Results from a pharmacokinetics analysis of samples taken from the patient as described in Example 2 are shown in FIG. 1.

Example 4—Flow Cytometric (FACS) Examination of Blood Lineage Subsets

Figure 2A:
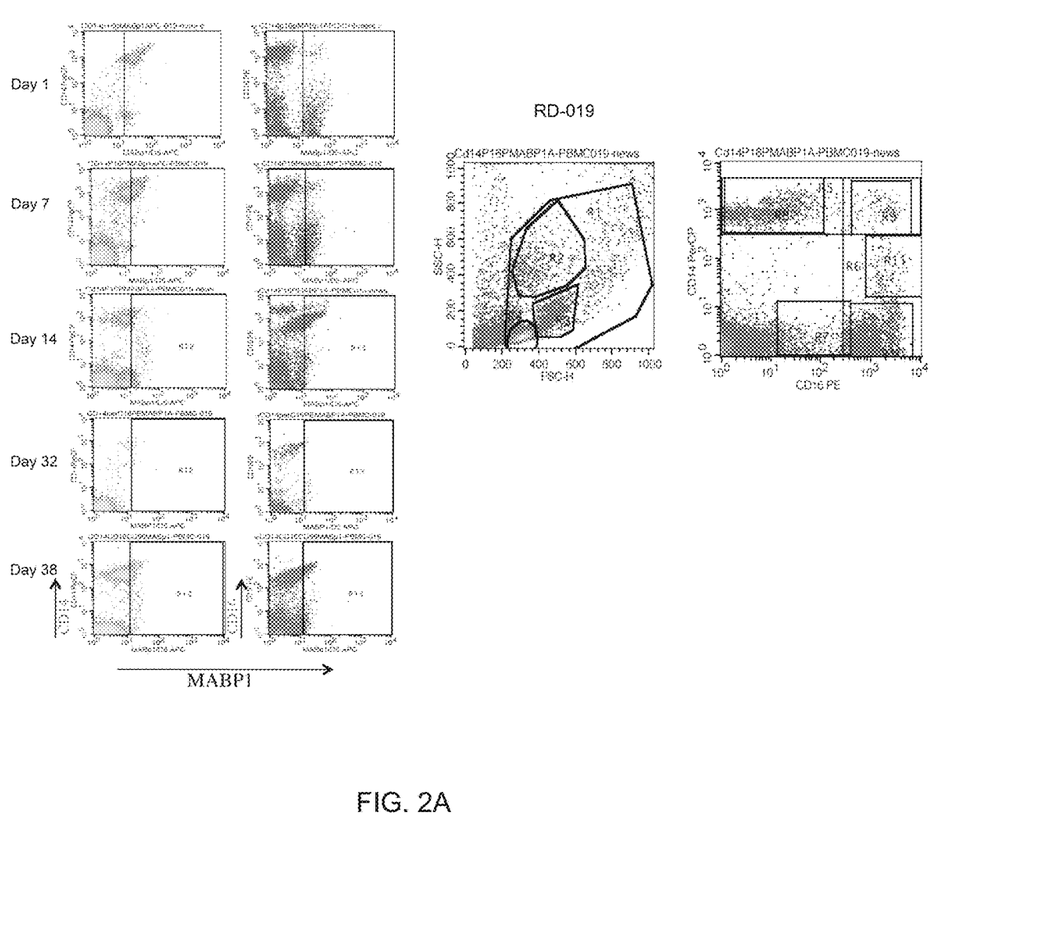
FIGS. 2A, 2B, and 2C show a series of graphs and histograms showing flow cytometric blood analyses after administration of MABp1 to a human subject with reactive arthritis.
Figure 2B:
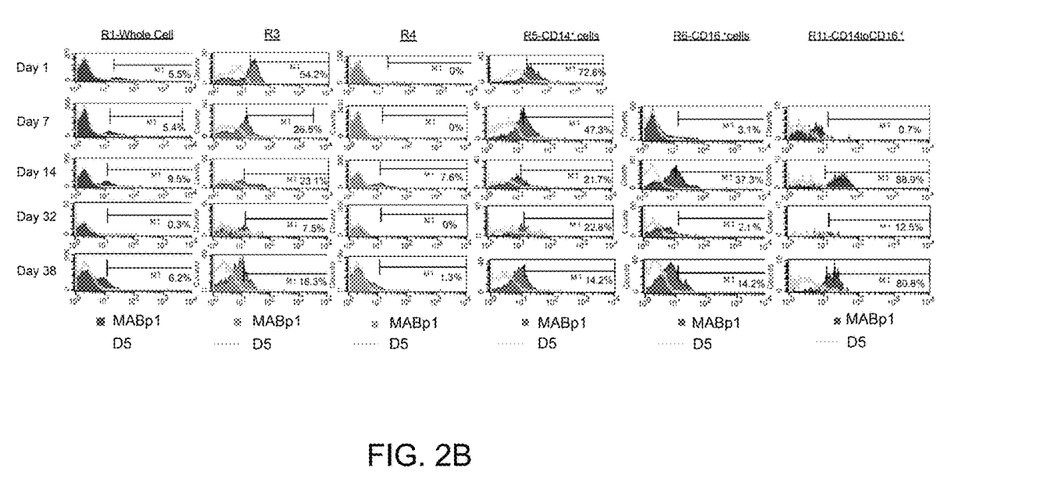
Figure 2C:
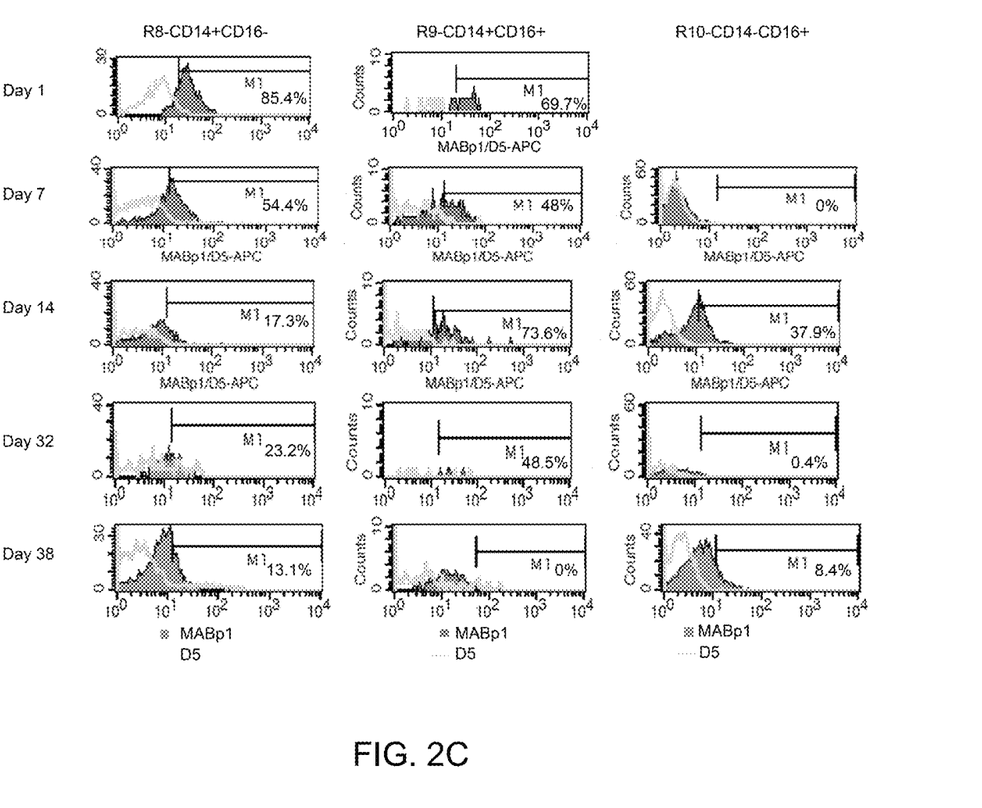
Figure 3:
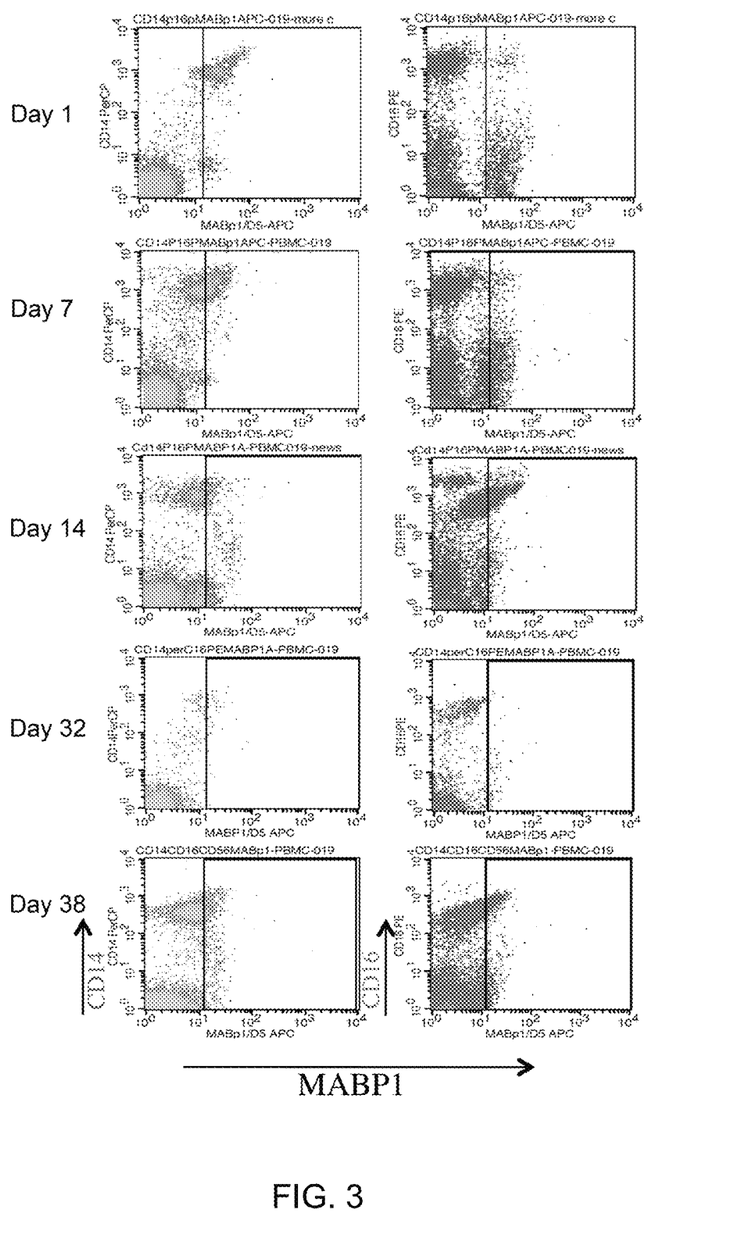
FIG. 3 is a series of graphs showing flow cytometric blood analyses after administration of MABp1 to a human subject with reactive arthritis.

FACS procedures are described for both whole blood staining, and staining of peripheral blood mononuclear cells (PBMC) enriched from whole blood. Both whole blood and PBMC staining was performed on all samples. This FACS analysis allows relative percentage determination of blood lineage subsets: B and T lymphocytes, NK cells, monocytes, neutrophils, and IL-1α+ cells. Results from FACs analyses of samples taken from the patient as described in Example 2 are shown in FIGS. 2 and 3. A photomicrograph of a blood smear showed that MABp1 administration caused extensive vacuolization in peripheral blood monocytes when analyzed 32 days post administration.

Example 5—Treatment of Uveitis with an IL-1α-Specific Monoclonal Antibody

About two months following resolution of the uveitis described in Example 2, the patient experienced another episode of uveitis (predominantly iritis). The patient was started on corticoseroid and non-steroidal anti-inflammatory drops (NSAIDS). Oral NSAIDS were also used. The uveitis was unresponsive to treatment and progressed. However, there was no evidence of any joint involvement, with shoulder continuing to show improvement in mobility. The patient was administered MABp1 topically to the affected eye. MABp1 (15 mg/ml solution) was administered at a rate of one drop per minute, for ten minutes, for a total of ten drops to the affected eye (approximately 3.75 mg in 0.25 ml). The patient did not complain of any pain during the administration. However, for several hours after, the patient reported discomfort and burning. Oral NSAIDs were taken and the patient slept. The next morning, the patient reported considerable improvement, reduced pain and less inflammation than prior to administration. Twenty-four hours after the first administration of the MABP1 drops, the patient administered 10 drops in the same fashion. Again, discomfort and burning was noted. Oral NSAIDs were taken, and again the patient took bed rest. The uveitis resolved itself completely. No further medications were taken. No recurrence of uveitis was observed over the next four months.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing CD14+IL-1α+ peripheral blood monocytes in a human subject in need of a treatment of arthritis, comprising subcutaneously administering to the human subject a pharmaceutical composition comprising a pharmaceutically acceptable carrier and the IL-1α-specific monoclonal antibody MABp1 at a dosage of 0.2 to 20 mg/kg body weight, wherein administration of the pharmaceutical composition decreases the number of CD14+IL-1α+ peripheral blood monocytes in the human subject by at least 5%.

2. The method of claim 1, wherein the pharmaceutical composition is administered to the subject more than once.

3. The method of claim 1, wherein the human subject has no detectable CD14+IL-1α+ peripheral blood monocytes as measured by flow cytometric analysis of blood sample taken from the human subject after the administration of the pharmaceutical composition.

4. A method of treating arthritis in a human subject in need thereof, the method comprising subcutaneously administering to the human subject a pharmaceutical composition comprising a pharmaceutically acceptable carrier and the monoclonal antibody MABp1 at a dosage of 0.2 to 20 mg/kg body weight, wherein the human subject has reduced pain associated with the arthritis after the treatment.

5. The method of claim 4, wherein the administration ameliorates joint inflammation in the subject.

6. The method of claim 4, wherein the human subject has no detectable CD14+IL-1α+ peripheral blood monocytes as measured by flow cytometric analysis of blood sample taken from the human subject after the administration of the pharmaceutical composition.

7. The method of claim 4, wherein the pharmaceutical composition is administered to the human subject more than once.

* * * * *